United States Patent [19]

Yamada et al.

[11] Patent Number: 5,731,209
[45] Date of Patent: Mar. 24, 1998

[54] METHOD FOR THE DETERMINATION OF NITROGEN CONCENTRATION IN COMPOUND SEMICONDUCTOR

[75] Inventors: Masato Yamada; Munehisa Yanagisawa; Susumu Higuchi, all of Gunma-ken, Japan

[73] Assignee: Shin-Etsu Handotai Co., Ltd., Tokyo, Japan

[21] Appl. No.: 614,206

[22] Filed: Mar. 12, 1996

[30] Foreign Application Priority Data

Mar. 15, 1995 [JP] Japan ................................. 7-055509

[51] Int. Cl.$^6$ ................................................. G01N 21/59
[52] U.S. Cl. .......................... 436/106; 436/114; 436/164
[58] Field of Search ............................. 436/106, 114, 436/164

[56] References Cited

PUBLICATIONS

Lightowlers, E.C. et al. "Nitrogen Concentration in GaP Measured by Optical Absorption and by Proton–induced Nuclear Reactions" Journal of Applied Physics, vol. 45, No. 5 (May 1974) pp. 2191–2200.

Thierry–Mieg, V. et al. "Determination of the nitrogen doping of liquid phase epitaxy GaP and alloys by optical absorption and photoluminescence" J. Appl. Phys., vol. 54, No. 9 (Sep. 1983) pp. 5358–5362.

Riede, V. et al. "Nitrogen Concentration in GaP:N Epitaxial Layers from Localized Mode Absorption Measurments" Physica Status Solidi (a), vol. 89, No. 2, (Jun. 1985) pp. K147–K151.

Donecker, J. et al., Proceedings of the International Conference Radiative Recombination in III–V Compound Semiconductors, (1979) pp. 43–47.

Yu, R., Journal of Xiamen University Natural Science, (1992) pp. 152–155.

Lupal et al., "Determination of the Nitrogen Concentration in Epitaxial Layers of GAASP by the Optical Method", *Inorganic Materials*, vol. 22, No. 2, 1986, pp. 157–161.

Kloth et al., "Determination of the Nitrogen Concentration in VPE–GAASP", *Physica Status Solidi A.*, vol. 100, No. 2, 1987, pp. 545–552.

Hansel et al., "Determination of Nitrogen Concentration in GAP Epitaxial Layers by Two Independent Methods", *Kristall Und Technik*, vol. 14, No. 8, 1979, pp. 977–984.

Thomas et al., "Isoelectronic Traps Due to Nitrogen in Gallium Phosphide", *Physical Review*, vol. 150, No. 2, 1966, pp. 680–689.

*Primary Examiner*—Jeffrey Snay
*Attorney, Agent, or Firm*—Wenderoth, Lind & Ponack

[57] ABSTRACT

An efficient method is proposed for the determination of the concentration of nitrogen in an indirect-transition compound semiconductor such as gallium phosphide added as an isoelectronic trap. The method utilizes the fact that a good correlation of proportionality is held between the nitrogen concentration and the difference $\Delta\alpha(=\alpha_N-\alpha)$ in the absorption coefficient of light of a wavelength identical with the wavelength $\lambda_N$ due to the excitons under constraint in the isoelectronic trap between the semiconductors with ($\alpha_N$) and without ($\alpha$) addition of nitrogen. A working curve is presented between the nitrogen concentration determined by the method of SIMS and the value of $\Delta\alpha$.

6 Claims, 3 Drawing Sheets

METHOD FOR THE DETERMINATION OF NITROGEN CONCENTRATION IN COMPOUND SEMICONDUCTOR

BACKGROUND OF THE INVENTION

The present invention relates to a method for the determination of the concentration of nitrogen in a compound semiconductor. More particularly, the invention relates to a method for the determination of the concentration of nitrogen introduced into the epitaxial growth layer of a III–V Group compound semiconductor of the indirect-transition type as an isoelectronic trap dopant.

It is conventional practice in a light-emitting diode by using an indirect-transition type III–V Group compound semiconductor such as gallium phosphide GaP, gallium arsenide phosphide $GaAs_{1-x}P_x$, in which the subscript x is a number larger than 0.45 but smaller than 1.0, and the like that the light-emitting efficiency is enhanced by introducing nitrogen into the epitaxial growth layer of the compound semiconductor to serve as an isoelectronic trap or, namely, a light-emitting center because the light-emitting efficiency cannot be high enough by the mere formation of a p–n junction. In a light-emitting diode using an indirect-transition type III–V Group compound semiconductor as the material, accordingly, one of the important factors having influences on the light-emitting characteristics such as brightness, wavelength and the like is the concentration of nitrogen therein introduced as an isoelectronic trap.

Different from ordinary donors or acceptors, the behavior of nitrogen as an isoelectronic dopant is not electric so that no electric means are applicable to the determination of nitrogen concentration. Therefore, known methods for the determination of the nitrogen concentration heretofore practiced include the method of secondary-ion mass spectrometry, referred to as SIMS hereinafter, the method reported in Journal of Applied Physics, volume 45 (1974), No. 5, page 2191, in which the concentration of nitrogen is obtained from the absorption coefficient of the light of the wavelength corresponding to the transition energy of the nitrogen trap or the isoelectronic trap, and so on.

Of the above described two methods for the determination of the nitrogen concentration, the former method of SIMS is a destructive method which is performed by destroying the sample and, in addition, a considerably long time is taken therein for a single run of the determination before a result is obtained so that this method is not simple and efficient and not suitable as a method for process inspection.

The latter method also has several problems and disadvantages although this method is non-destructive. Namely, the nitrogen concentration is obtained in this method from the coefficient of correlation between the absorption coefficient at the absorption wavelength by the excitons under constraint by the isoelectronic trap or nitrogen trap and the absorption coefficient at the absorption wavelength by free excitons so that the measurement must be conducted at an extremely low temperature such as 4.2K, which is the temperature of liquid helium, in order to detect the absorption by the free excitons.

Further, the applicability of this method is limited and, although this method is applicable to those samples in which the distribution of the isoelectronic traps is uniform such as, for example, bulk crystals in which the distribution of nitrogen atoms as the isoelectronic traps is relatively uniform, an extremely great difficulty is encountered relative to the low accuracy of measurement when this method is applied to a multi-layered compound semiconductor consisting of both of an indirect-transition III–V Group compound semiconductor with addition of nitrogen and a compound semiconductor of the same type without addition of nitrogen such as an epitaxial wafer of the said compound semiconductor.

SUMMARY OF THE INVENTION

The present invention accordingly has an object to provide, in view of the above described problems and disadvantages in the prior art methods, a novel and efficient non-destructive method for the determination of the nitrogen concentration in an indirect-transition III–V Group compound semiconductor or, in particular, in an epitaxially grown layer of the same compound semiconductor with high accuracy.

Thus, the method of the present invention for the determination of the concentration of nitrogen added to an indirect-transition III–V Group compound semiconductor as an isoelectronic trap comprises the steps of:

(a) obtaining the difference $\Delta\alpha$, which is equal $\alpha_N-\alpha$, between the absorption coefficient $\alpha_N$ of the indirect-transition III–V Group compound semiconductor with addition of nitrogen to an incident light of the wavelength identical with or close to the absorption wavelength $\lambda_N$ by the excitons under constraint in the isoelectronic traps and the absorption coefficient $\alpha$ of the same compound semiconductor without addition of nitrogen; and (b) determining the nitrogen concentration from the known correlation between the nitrogen concentration in the same compound semiconductor and the difference $\Delta\alpha$.

DETAILED DESCRIPTION OF THE PREFERRED EMBODIMENTS

As is described above, the present invention provides a non-destructive method for the determination of the concentration of nitrogen added to an indirect-transition III–V Group compound semiconductor as an isoelectronic trap which comprises the steps of:

(a) obtaining the difference $\Delta\alpha$, which is equal to $a_N-\alpha$, between the absorption coefficient $\alpha_N$ of the indirect-transition III–V Group compound semiconductor with addition of nitrogen to an incident light of the wavelength identical with or close to the absorption wavelength $\lambda_N$ by the excitons under constraint in the isoelectronic traps and the absorption coefficient $\alpha$ of the same compound semiconductor without addition of nitrogen; and (b) determining the nitrogen concentration from the known cor-relation between the nitrogen concentration in the same compound semiconductor and the difference $\Delta\alpha$.

This method is applicable to the III–V Group compound semiconductors including gallium phosphide GaP and gallium arsenide phosphide $GaAs_{1-x}P_x$, in which x is a number in the range from 0.45 to 1.0.

The above mentioned difference $\Delta\alpha$ in the absorption coefficients can be obtained by the equation (1) given below:

$$\Delta\alpha = -ln(I_N/I)/t, \quad (1)$$

in which t is the thickness of the above mentioned compound semiconductor layer in cm. $I_N$ is the intensity of the transmitting light through the above mentioned compound semiconductor layer with addition of nitrogen when the intensity of the incident light is $I_0$ and I is the intensity of the transmitting light through the above mentioned compound semiconductor layer without addition of nitrogen when the intensity of the incident light is $I_0$.

Further, the above mentioned difference $\Delta\alpha$ in the absorption coefficients can be obtained also by the equation (2) given below:

$$\Delta\alpha = -ln(I_N/I')/t, \quad (2)$$

in which is the thickness of the above mentioned compound semiconductor layer with addition of nitrogen in cm. $I_N$ is the intensity of the transmitting light through the above mentioned compound semiconductor multilayer at a wavelength $\lambda_N$ or a wavelength close to the above mentioned absorption wavelength $\lambda_N$ in the absorption spectrum of the compound semiconductor when the intensity of the incident light is $I_0$ and I' is the intensity of the transmitting light at a wavelength $\lambda_N$ or a wavelength close to the above mentioned absorption wavelength $\lambda_N$ on the extrapolation line of the above mentioned absorption spectrum from the longer wavelength side.

In the following, the present invention is described in more detail by way of an example.

Figure 3A:
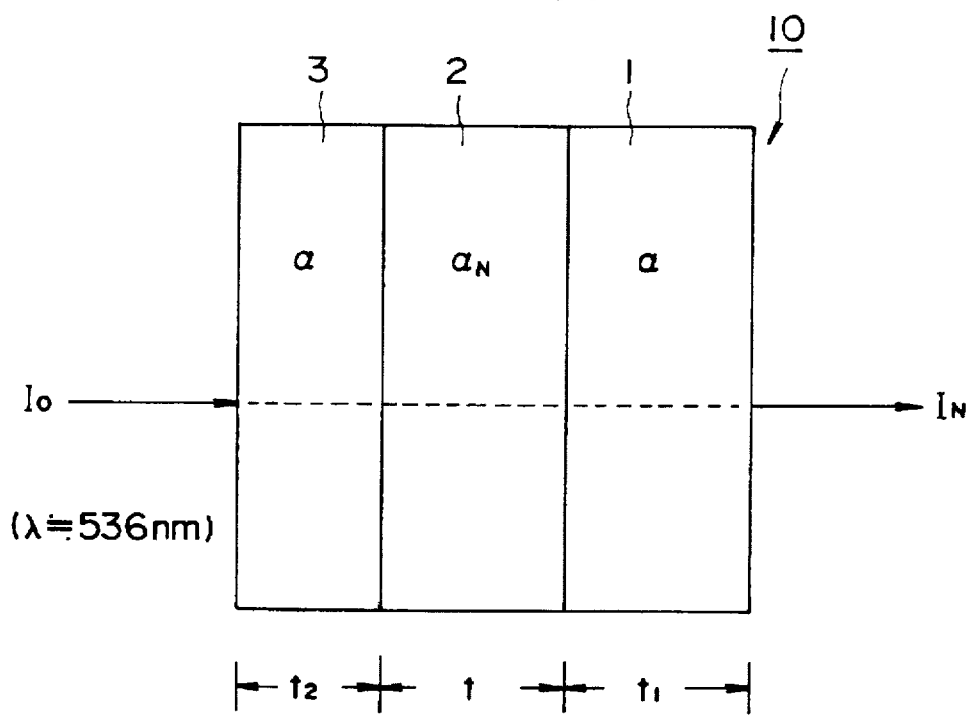
FIGS. 3A and 3B are each a schematic cross sectional view of a gallium phosphide epitaxial wafer having an n-type gallium phosphide layer with and without addition of nitrogen, respectively.
Figure 3B:
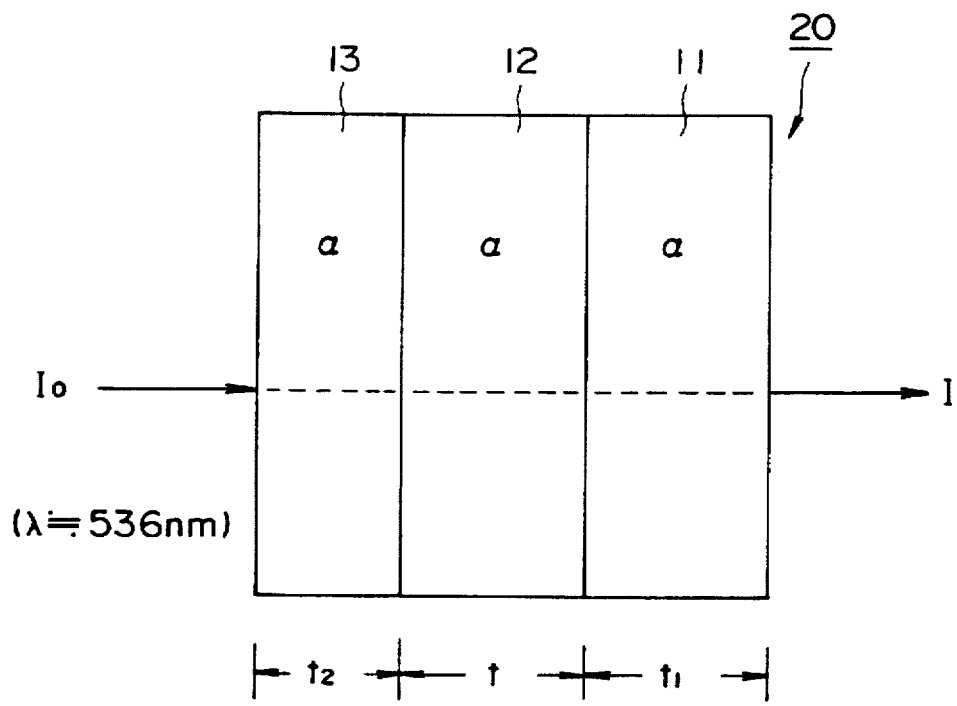

In the first place, the gallium phosphide epitaxial wafer illustrated in FIGS. 3A and 3B by a vertical cross sectional view is taken as an example for the description of the method to obtain the above mentioned difference in the absorption coefficients denoted by $\Delta\alpha$.

The wafer 10 illustrated in FIG. 3A is a gallium phosphide epitaxial wafer, referred to as GaP EpW(N) hereinafter, consisting of a substrate 1 of n-type gallium phosphide and laminating layers successively formed thereon including an n-type gallium phosphide layer 2 with addition of nitrogen and a p-type gallium phosphide layer 3. Further, the wafer 20 illustrated in FIG. 3B is a gallium phosphide epitaxial wafer, referred to as GaP EpW(0) hereinafter, having the same laminated structure as in the above mentioned GaP EpW(N) except that the n-type gallium phosphide layer 12 formed on the substrate 11 is without addition of nitrogen, the layer 13 being the same as the layer 3.

In FIGS. 3A and 3B, $I_0$ is the intensity of the incident light and $I_N$ and I are each the intensity of the transmitting light through the epitaxial wafers 10 and 20, respectively, while $\alpha_N$ and $\alpha$ are each the absorption coefficient of gallium phosphide with and without addition of nitrogen, respectively.

When, in this arrangement, the temperature of measurement is set at the temperature of liquid nitrogen, i.e. 77K, and the wavelength of the light used is in the vicinity of 536 nm which is the absorption wavelength $\lambda_N$ by the exciton under constraint in the nitrogen trap at the temperature of liquid nitrogen, i.e. 77K, the absorption coefficients of the gallium phosphide layers 1 and 3 in FIG. 3A and 11, 12 and 13 in FIG. 3B without addition of nitrogen are each substantially identical with the others to be $\alpha$. This fact can be experimentally confirmed.

According to the Lambert-Beer's law, $I_N$ and I are each expressed approximately by the following equations (3) and (4), respectively:

$$I_n = I_0 exp[-\alpha(t_1+t_2)-\alpha_N \cdot t]; \quad (3)$$

and $$I = I_0 exp[-\alpha(t_1+t_2+t)]. \quad (4)$$

Combination of these equations (3) and (4) leads to the above given equation (1):

$$\Delta\alpha = (\alpha_N - \alpha) = -ln(I_N/I)/t.$$

By the measurement of the intensities $I_N$ and I of the transmitting light, accordingly, the above given equation (1) gives the difference $\Delta\alpha$ between the absorption coefficient $\alpha_N$ of the gallium phosphide layer 2 with addition of nitrogen and the absorption coefficient $\alpha$ of the gallium phosphide layer 12 without addition of nitrogen at the wavelength of 536 nm.

Figure 4A:
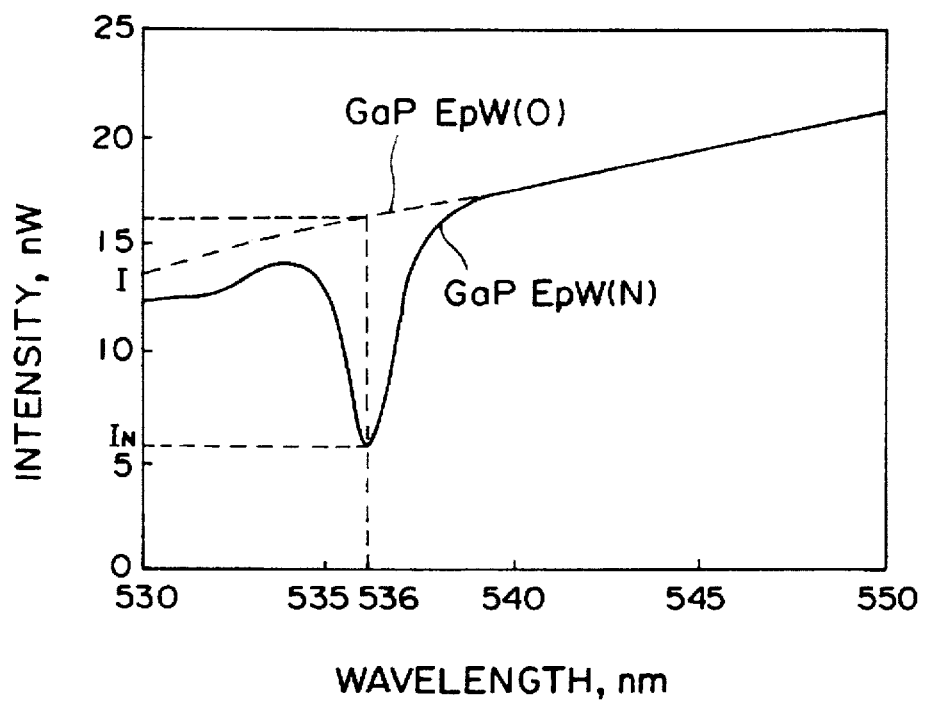
FIG. 4A shows absorption spectra of the epitaxial wafers illustrated in FIG. 3A (solid line curve) and in FIG. 3B (broken line curve).

FIG. 4A of the accompanying drawing shows examples of the absorption spectra of the GaP EpW(N) and GaP EpW(0) illustrated in FIGS. 3A and 3B, respectively, by the solid line curve and broken line curve, respectively, taking the wavelength of the incident light on the abscissa axis and the intensity of the transmitting light on the ordinate axis. These absorption spectra were measured at the temperature of liquid nitrogen, i.e. 77K. Thus, the value of $\Delta\alpha$ can be obtained from the equation (1) with substitution of the intensity values $I_N$ and I of the transmitting light in each at the absorption wavelength 536 nm by the excitons under constraint in the isoelectronic trap or nitrogen trap.

Figure 4B:
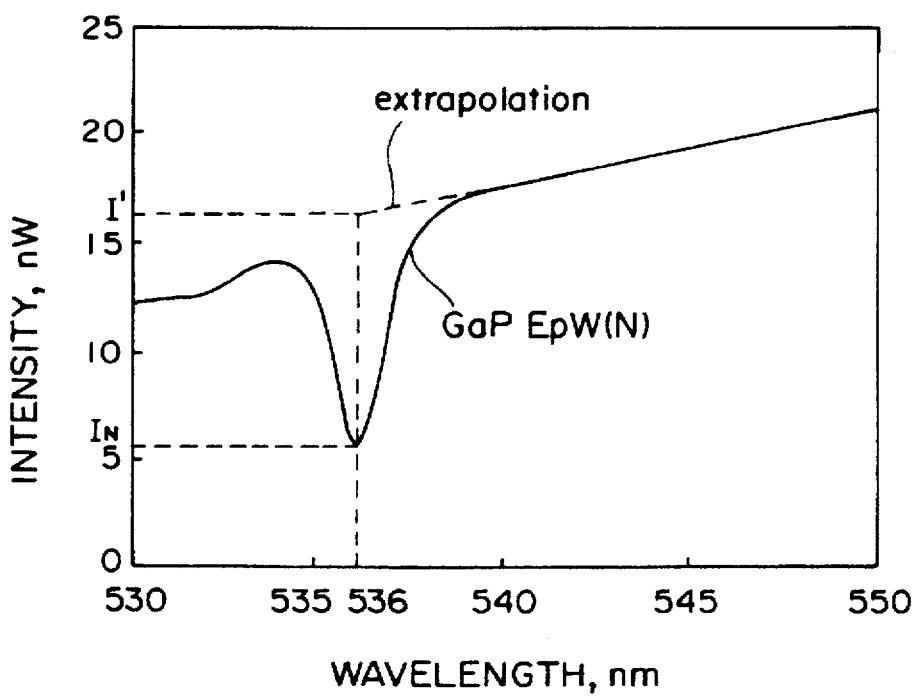
FIG. 4B shows an extrapolation of the spectrum shown by the solid line curve of FIG. 4A from the longer wavelength side.

As is clear from FIG. 4A, furthermore, the absorption spectra of the above mentioned GaP EpW(N) and GaP EpW(0) approximately coincide each with the other in the wavelength region of 540 nm or longer of the incident light. As is shown in FIG. 4B, the intensity I' of the transmitting light at a wavelength approximately equal to the absorption wavelength 536 nm by the excitons on the extrapolation line of the absorption spectrum GaP EpW(N), which is a reproduction of the GaP EpW(N) spectrum in FIG. 4A, from the longer wavelength side coincides approximately with the intensity I of the transmitting light in the above mentioned GaP EpW(0) at the same wavelength. Accordingly, the value of $\Delta\alpha$ can be obtained approximately from the equation (2) given below by the substitution of the values of the above mentioned $I_N$ and I':

$$\Delta\alpha = -ln(I_N/I')/t. \quad (2)$$

This way for the determination of $\Delta\alpha$ is very efficient because what is required therefor is only a gallium phosphide epitaxial wafer having a gallium phosphide layer with addition of nitrogen and a gallium phosphide layer without addition of nitrogen.

The above described method for the determination of the nitrogen concentration in the gallium phosphide layer is applicable also to other indirect-transition III–V Group compound semiconductors.

For example, it is established that a correlation with sufficiently high accuracy is held also in a gallium arsenide phosphide of formula $GaAs_{1-x}P_x$, in which x is a number from 0.45 to 1.0, between the value of $\Delta\alpha$ obtained by using the absorption wavelength $\lambda_N$ by the excitons under constraint in the nitrogen trap corresponding to the respective value of x and the concentration of nitrogen determined by the method of SIMS so that this correlation can be utilized for the determination of the nitrogen concentration from $\Delta\alpha$.

The sample used in an example of the method of the present invention should have a structure of the epitaxial wafer illustrated in FIGS. 3A and 3B. The sample 10 having a structure illustrated in FIG. 3A is a GaP EpW(N) prepared by successively laminating, on the n-type gallium phosphide substrate 1 having a thickness $t_1$ of about 300 μm, an n-type gallium phosphide layer 2 having a thickness t of about 37 μm with addition of nitrogen and a p-type gallium phosphide layer 3 having a thickness $t_2$ of about 50 μm each by the liquid epitaxial growth method. The sample 20 having a structure illustrated in FIG. 3B is a GaP EpW(0) prepared by successively laminating, on the n-type gallium phosphide substrate 11 having a thickness $t_1$ of about 300 μm, an n-type gallium phosphide layer 12 having a thickness t of about 37 μm without addition of nitrogen and a p-type gallium phosphide layer 13 having a thickness $t_2$ of about 50 μm each by the liquid phase epitaxial growth method.

Figure 2:
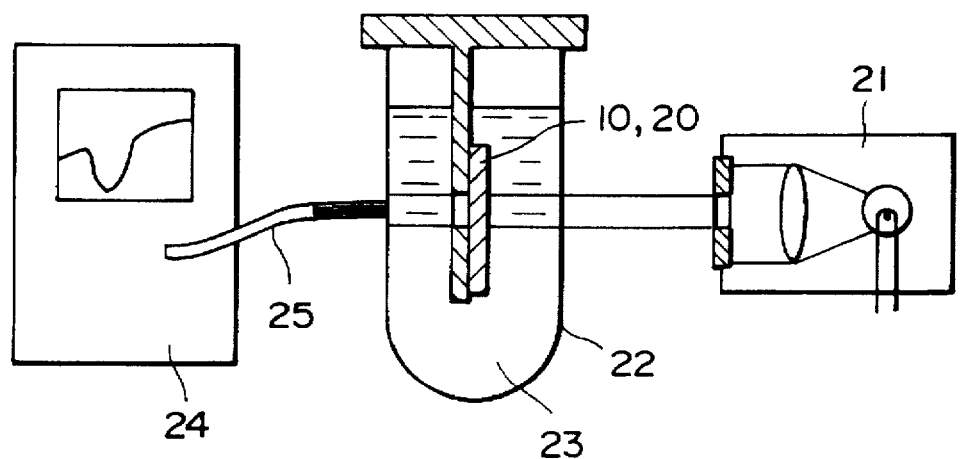
FIG. 2 is a schematic illustration of the apparatus for the measurement of light absorption according to the inventive method.

FIG. 2 is a schematic illustration of an apparatus used in the measurement according to the inventive method. The above described sample 10 or 20 for the measurement held in a Dewar flask 22 filled with liquid nitrogen 23 is irradiated by the light coming from the light source 21 and the transmitting light is introduced into the spectrum analyzer 24 by way of the optical fiber 25. Measurement was conducted in the above described arrangement of the apparatus with a light having a wavelength of 536 nm and keeping the sample 10 or 20 at the temperature of liquid nitrogen 23, i.e. 77K, to determine the intensities of the transmitting light $I_N$ and I by the spectrum analyzer 24 and the difference in the absorption coefficient $\Delta\alpha$ was calculated from the equation (1) by the substitution of the values of $I_N$ and I.

Figure 1:
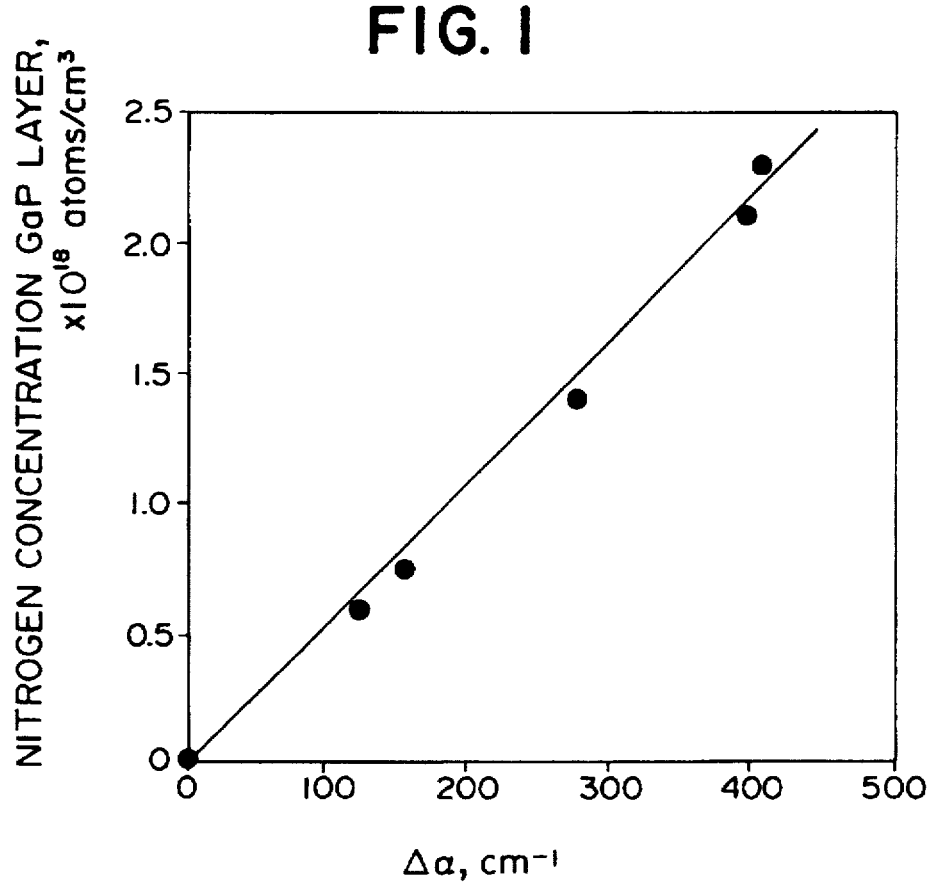
FIG. 1 is a graph showing the value of $\Delta\alpha$ in $cm^{-1}$ of a gallium phosphide wafer as a function of the concentration of nitrogen in $atoms/cm^3$ in a gallium phosphide layer determined by the method of SIMS measurement.

Determination of the value of $\Delta\alpha$ was conducted in the above described manner for several samples of epitaxial wafers GaP EpW(N) 10 having varied nitrogen concentrations in the n-type gallium phosphide layer 2 and the thus obtained values of $\Delta\alpha$ were plotted on a graph as a function of the nitrogen concentration in atoms/cm$^3$ in the epitaxial layer 2 determined by the method of SIMS to obtain a good straight line passing through the origin as is shown in FIG. 1.

As is understood from FIG. 1, a correlation of very high accuracy is held between the value of $\Delta\alpha$ and the nitrogen concentration so that the graph of FIG. 1 can be utilized as a working curve for the determination of the nitrogen concentration from the value of $\Delta\alpha$ which can be obtained easily and conveniently as is described above.

As is shown in FIGS. 4A and 4B, good coincidence with an accuracy of ±5% was obtained from the absorption spectrum of the wafer GaP EpW(N) 10 between the intensity I' of the transmitting light having a wavelength of 536 nm as the extrapolated value on the extrapolation line from the longer wavelength side and the intensity I of the transmitting light in the sample wafer GaP EpW(0). As a conclusion, therefore, the value of $\Delta\alpha$ can be obtained approximately by using the above mentioned $I_N$ and I' determined for the GaP EpW(N).

As is described above, a good correlation with very high accuracy is established between the value of $\Delta\alpha$ and the nitrogen concentration in the indirect-transition III–V Group compound semiconductors to provide a very efficient and convenient means for the determination of the nitrogen concentration therein. Further advantages obtained by the inventive method consist in that the method is non-destructive, the measurement can be performed at a relatively high temperature of liquid nitrogen without necessitating an extremely low temperature obtained only by using liquid helium, the apparatus used in the measurement has a simple structure and is easy to handle and the measurement can be performed within a short time so that the inventive method can be used as a routine in-process inspection method of indirect-transition III–V Group compound semiconductors.

What is claimed is:

1. A method for the determination of the concentration of nitrogen added to an indirect-transition III–V Group compound semiconductor as an isoelectronic trap which comprises the steps of:

(a) obtaining the difference $\Delta\alpha$, which is equal to $\alpha_N-\alpha$, between the absorption coefficient $\alpha_N$ of the indirect transition III–V Group compound semiconductor with addition of nitrogen to an incident light of the wavelength identical with the absorption wavelength $\lambda_N$ by the excitons under constraint in the isoelectronic traps and the absorption coefficient $\alpha$ of the same compound semiconductor without addition of nitrogen; and (b) determining the nitrogen concentration from the known correlation between the nitrogen concentration in the same compound semiconductor and the difference $\Delta\alpha$.

2. The method for the determination of the concentration of nitrogen added to an indirect-transition III–V Group compound semiconductor as claimed in claim 1 in which the difference $\Delta\alpha$ is obtained by calculation from the equation:

$$\Delta\alpha = -ln(I_N/I)/t,$$

in which t is the thickness of the compound semiconductor in cm, $I_N$ is the intensity of the transmitting light through the compound semiconductor with addition of nitrogen and I is the intensity of the transmitting light through the compound semiconductor without addition of nitrogen, the intensity of the incident light being identical and the incident light having a wavelength of $\lambda_N$.

3. The method for the determination of the concentration of nitrogen added to an indirect-transition III–V Group compound semiconductor as claimed in claim 1 in which the compound semiconductor with addition of nitrogen is in the form of a layer forming a multilayered compound semiconductor wafer together with a layer of the same compound semiconductor without addition of nitrogen and the difference $\Delta\alpha$ is obtained by calculation from the equation:

$$\Delta\alpha = -ln(I_N/I')/t,$$

in which t is the thickness of the layer of the compound semiconductor with addition of nitrogen in cm, $I_N$ is the intensity of the transmitting light through the multilayered compound semiconductor wafer on an absorption spectrum, the incident light having a wavelength of $\lambda_N$, and I' is the intensity of the transmitting light on an extrapolation line of the absorption spectrum from the longer wavelength side corresponding to the wavelength $\lambda_N$.

4. A method for the determination of the concentration of nitrogen added to an indirect-transition III–V Group compound semiconductor as an isoelectronic trap which comprises the steps of:

(a) obtaining the difference $\Delta\alpha$, which is equal to $a_N-\alpha$, between the absorption coefficient $\alpha_N$ of the indirect-transition III-V Group compound semiconductor with addition of nitrogen to an incident light of the wavelength close to the absorption wavelength $\lambda_N$ by the excitons under constraint in the isoelectronic traps and the absorption coefficient $\alpha$ of the same compound semiconductor without addition of nitrogen; and (b) determining the nitrogen concentration from the known correlation between the nitrogen concentration in the same compound semiconductor and the difference $\Delta\alpha$.

5. The method for the determination of the concentration of nitrogen added to an indirect-transition III-V Group compound semiconductor as claimed in claim 4 in which the difference $\Delta\alpha$ is obtained by calculation from the equation:

$$\Delta\alpha = -ln(I_N/I)/t,$$

in which t is the thickness of the compound semiconductor in cm, $I_N$ is the intensity of the transmitting light through the compound semiconductor with addition of nitrogen and I is the intensity of the transmitting light through the compound semiconductor without addition of nitrogen, the intensity of the incident light being identical and the incident light having a wavelength close to $\lambda_N$.

6. The method for the determination of the concentration of nitrogen added to an indirect-transition III-V Group compound semiconductor as claimed in claim 4 in which the compound semiconductor with addition of nitrogen is in the form of a layer forming a multilayered compound semiconductor wafer together with a layer of the same compound semiconductor without addition of nitrogen and the difference $\Delta\alpha$ is obtained by calculation from the equation:

$$\Delta\alpha = -ln(I_N/I')/t,$$

in which t is the thickness of the layer of the compound semiconductor with addition of nitrogen in cm, $I_N$ is the intensity of the transmitting light through the multilayered compound semiconductor wafer on an absorption spectrum, the incident light having a wavelength close to $\lambda_N$, and I' is the intensity of the transmitting light on an extrapolation line of the absorption spectrum from the longer wavelength side corresponding to the wavelength close to $\lambda_N$.

* * * * *